US005538599A

United States Patent [19]
Wong et al.

[11] Patent Number: 5,538,599
[45] Date of Patent: Jul. 23, 1996

[54] PHENOL SEPARATION

[75] Inventors: Tim T. Wong, Downingtown; Stephen H. Harris, Kennett Square; Thomas S. Zak; Te Chang, both of West Chester, all of Pa.

[73] Assignee: ARCO Chemical Technology, L.P., Greenville, Del.

[21] Appl. No.: 463,833

[22] Filed: Jun. 5, 1995

[51] Int. Cl.$^6$ .................................................. B01D 3/40
[52] U.S. Cl. .................. 203/58; 203/78; 203/80; 203/DIG. 16; 568/754; 568/810; 568/913
[58] Field of Search .................................. 203/57, 58, 78, 203/80, DIG. 16; 568/913, 810, 754; 210/664, 670; 549/542

[56] References Cited

U.S. PATENT DOCUMENTS

| | | |
|---|---|---|
| 2,551,584 | 5/1951 | Carlson et al. ............................ 203/58 |
| 3,351,635 | 11/1967 | Kollar . |
| 3,919,078 | 11/1975 | Cohen et al. ............................ 208/321 |
| 4,012,289 | 3/1977 | Haskell ..................................... 203/58 |
| 4,021,490 | 5/1977 | Hudson ..................................... 203/58 |
| 5,171,868 | 12/1992 | Albal et al. . |
| 5,320,715 | 6/1994 | Berg ......................................... 203/58 |
| 5,334,774 | 8/1994 | Kogure et al. ........................... 568/754 |

FOREIGN PATENT DOCUMENTS

| | | | |
|---|---|---|---|
| 0448898 | 6/1948 | Canada ................................. 208/325 |
| 1392735 | 4/1975 | United Kingdom ..................... 203/58 |

*Primary Examiner*—Virgina Manoharan
*Attorney, Agent, or Firm*—William C. Long

[57] ABSTRACT

A process is provided whereby phenol is separated from 1-phenyl ethanol, acetophenone or mixtures by extractive distillation with sulfolane as extractive distillation agent which decreases phenol volatility relative to 1-phenyl ethanol and acetophenone.

2 Claims, 1 Drawing Sheet

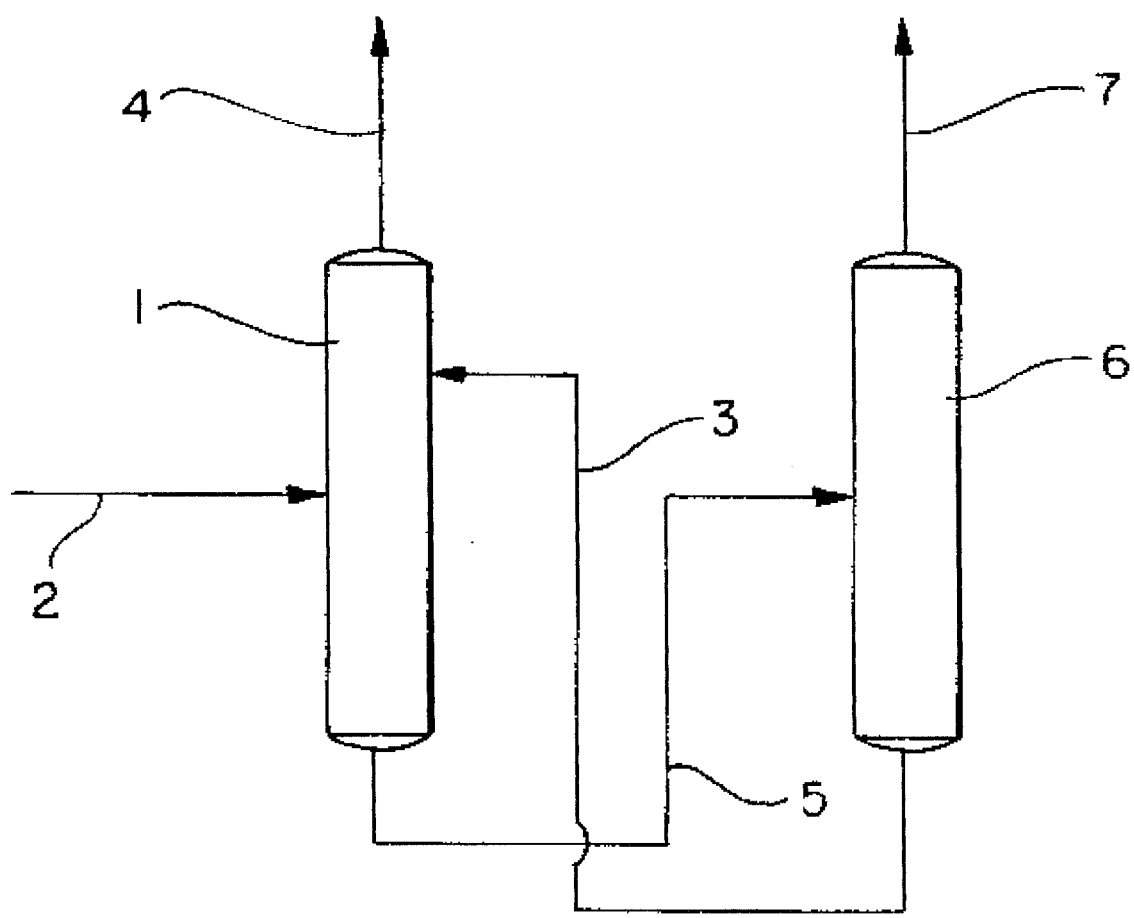

5,538,599

PHENOL SEPARATION

BACKGROUND OF THE INVENTION

1. Field of the Invention

In the Oxirane process for the co-production of propylene oxide and styrene monomer, propylene is reacted with ethylbenzene hydroperoxide to form propylene oxide and methyl benzyl alcohol (1-phenyl ethanol), and the methyl benzyl alcohol is dehydrated to styrene. Significant amounts of phenol are formed which, in accordance with the present invention are separated from methyl benzyl alcohol and associated acetophenone by extractive distillation with sulfolane as extractive distillation solvent.

2. Description of the Prior Art

An extremely successful process for the co-production of propylene oxide and styrene monomer involves the molecular oxygen oxidation of ethyl benzene to form ethyl benzene hydroperoxide, the catalytic reaction of the hydroperoxide with propylene to form propylene oxide and 1-phenyl ethanol, and the dehydration of the 1-phenyl ethanol to styrene monomer. The basic patent describing this process is U.S. Pat. No. 3,351,635.

There is formed in this process a stream comprised of 1-phenyl ethanol and acetophenone which also contains substantial amounts of phenol. It is important from the standpoint of product purity and yield that the phenol be removed.

Phenol separation can be accomplished by caustic treatment but this results in the formation of spent caustic waste streams which pose increasingly difficult problems of disposal. U.S. Pat. No. 5,171,868 provides a process whereby the amount of spent caustic to be disposed of can be substantially reduced. However, further improvements would be advantageous. Because of the close-boiling nature of the components, it is not economical to separate a mixture comprised of 1-phenyl ethanol, acetophenone and phenol by conventional distillation procedures.

BRIEF DESCRIPTION OF THE INVENTION

It has now been found that phenol can be separated from styrene precursors such as 1-phenyl ethanol and acetophenone by extractive distillation using sulfolane as extractive distillation agent thus greatly alleviating problems of spent caustic disposal.

BRIEF DESCRIPTION OF THE DRAWING

FIG. 1 illustrates schematically a practice of the invention.

DETAILED DESCRIPTION

In accordance with the present invention, styrene precursors including 1-phenyl ethanol, acetophenone and mixtures which contain contaminating amounts of phenol are extractively distilled with sulfolane as extractive distillation solvent thus decreasing the volatility of phenol relative to 1-phenyl ethanol and acetophenone whereby the phenyl ethanol and acetophenone can be distilled overhead from phenol-containing sulfolane solvent.

The mixtures treated in accordance with the invention generally comprise by weight about 0 to 99.9% 1-phenyl ethanol, about 0 to 99.9% acetophenone, and about 0.01 to 50% phenol. Minor amounts of other organic materials may also be present. Most advantageously, the mixtures treated in accordance with the invention are those produced by the Oxirane propylene oxide/styrene monomer process and comprise by weight about 20 to 90% 1-phenyl ethanol, about 10 to 75% acetophenone, about 0.5 to 5% phenol and about 1 to 20% other organics.

The relative volatilities of acetophenone, 1-phenyl ethanol and phenol are sufficiently close to make effective separation by conventional distillation excessively costly. However, by the extractive distillation procedure of the present invention, the separation is conveniently accomplished in an efficient and cost effective way.

Referring to the accompanying drawing, the phenol containing mixture to be purified is introduced into extractive distillation column 1 via line 2. Also introduced into column 1 at the upper section via line 3 is the sulfolane extractive distillation agent, i.e. tetramethylene sulfone.

The effect of the extractive distillation agent is to substantially decrease the phenol volatility relative to the other major components of the mixture, 1-phenyl ethanol and/or acetophenone, so that the 1-phenyl ethanol and acetophenone are separated overhead and removed via line 4. A bottoms stream containing the predominance of the phenol is removed via line 5 and passed to stripper 6. In stripper 6, the phenol is distilled overhead and recovered via line 7 while the extractive distillation agent is separated as a bottoms stream via line 3 and recycled to the extractive distillation column 1.

Through practice of the invention, substantially complete phenol separation can be accomplished without the need for caustic treatment with the accompanying problems of caustic waste stream disposal.

The extractive distillation can be carried out at conventional conditions in conventional distillation apparatus. Normally a distillation column having 10 to 30 theoretical stages can be used. Amounts of sulfolane ranging from about 50 to 200% by weight of the phenol containing feed are suitable.

Distillation of the 1-phenyl ethanol/acetophenone composition from the sulfolane mixture is conducted at 10–760 mm Hg pressure in column 1 of the drawing. Temperatures at these pressures range from 180°–390° F. Preferably the pressure is in the operating range from 10–30 mm Hg with temperatures in the overhead ranging from 180°–225° F.

Upon removal from the extractive distillation column, the phenol and sulfolane is stripped to separate phenol overhead with the bottoms sulfolane recycled to the extractive distillation column. The overhead conditions of the column is 180°–390° F. at 10–760 mm Hg. Preferably, the pressure is in the operating range from 10–30 mm Hg with temperatures in the overhead ranging from 180°–220° F.

The bottoms temperature of the two columns is dictated by the pressure drop of the system and the bubble point of the bottoms composition, wherein the stripper column reboiler operates at a higher overall temperature relative to the extractive distillation column reboiler at the same bottoms pressure.

Sulfolane as normally provided contains acidic impurities which would tend to catalyze dehydration of the 1-phenyl ethanol during the extractive distillation. In order to avoid this, it is especially advantageous to first treat the sulfolane with a basic ion exchange resin such as Rohm & Haas Amberlyst® A-21 prior to use in the extractive distillation. Amberlyst is a registered trademark of Rohm & Haas. As can be seen from the following table, treatment with basic ion exchange resin is effective in removing acidic components as manifested by the pH of a 50/50 by weight mixture of water and the treated sulfolane.

TABLE

| Sulfolane treatment | pH |
|---|---|
| As is | 2.88 |
| Basic resin (A-21) | 7.33 |
| Distillation heart cut | 3.12 |
| Distillation heart cut plus basic resin (A-21) | 7.39 |

In the advantageous basic ion exchange resin treatment the liquid sulfolane is contacted with solid resin at 30° to 70° C. Generally treatment with 4 volumes of resin per volume of sulfolane is sufficient. When activity has decreased substantially, the resin can be regenerated by treatment with base such as NaOH.

The following example illustrates the invention.

Referring to the accompanying drawing, a mixture comprised by weight of 24.8% 1-phenyl ethanol, 59.8% acetophenone, 3.1% phenol, and 13.3% other organics from the Oxirane process is fed at the rate of 1000 lbs/hr via line 2 to extractive distillation column 1, which has 18 theoretical stages, near the column midpoint. Also fed to column 1 near the upper end are 1000.47 lbs/hr. of sulfolane via line 3. The sulfolane had been treated with basic ion exchange resin Rohm & Haas A-21 to a pH of 7.33.

In column 1, acetophenone and 1-phenyl ethanol are extractively distilled from the phenol and are removed from column 1 at 192° F. and 20 mm Hg via line 4 at the rate of 999.56 lbs/hr. The removed 1-phenyl ethanol and acetophenone stream comprises by weight 0.3% phenol, 24.8% 1-phenyl ethanol, 58.9% acetophenone and 0% sulfolane and represents a suitable feed stream to the styrene producing section of an Oxirane plant.

A bottoms stream comprised of sulfolane and phenol is separated at 400° F. and 90 mm Hg via line 5 at the rate of 1028.54 lbs/hr. This stream comprises by weight 0% 1-phenyl ethanol, 0% acetophenone, 2.7% phenol, 0.1% other organics and 97.7% sulfolane and is passed via line 5 to stripper 6. In stripper 6, which has 11 theoretical stages, an overhead stream is removed at 185° F. and 20 mm Hg at the rate of 28.20 lbs/hr. This stream comprises by weight 0.9% 1-phenyl ethanol, 0.1% acetophenone, 98.9% phenol, 0% other organics and 0.1% sulfolane.

Sulfolane is separated at 380° F. and 65 mm Hg as bottoms and is recycled as above described via line 3 to extractive distillation column 1 Make up extractive distillation agent is added as needed (not shown).

From the above illustration, it can be seen that the present invention provides a convenient and effective method for phenol separation from 1-phenyl ethanol and/or acetophenone and thus provides a viable alternative to prior caustic treatment procedures.

We claim:

1. A method for the separation of phenol from 1-phenyl ethanol, acetophenone, or mixtures which comprises pretreating sulfolane which contains acidic impurities with a basic ion exchange resin so as to prevent catalytic dehydration of 1-phenyl ethanol during a subsequent distillation, separating sulfolane substantially free of acidic impurities from the ion exchange resin, extractively distilling a phenol containing stream of 1-phenyl ethanol and/or acetophenone with said separated sulfolane in amount of 50 to 200 wt. % of the phenol containing stream of 1-phenyl ethanol and/or acetophenone, separating 1-phenyl ethanol and acetophenone reduced in phenol overhead, and recovering phenol by distillation from the sulfolane extractive distillation agent.

2. The method of claim 1 wherein a mixture of 1-phenyl ethanol and acetophenone from a propylene oxide and styrene monomer process is extractively distilled from phenol.

* * * * *